US010370622B2

(12) United States Patent
Chandar et al.

(10) Patent No.: US 10,370,622 B2
(45) Date of Patent: *Aug. 6, 2019

(54) SOAP BAR HAVING ENHANCED ANTIBACTERIAL ACTIVITY

(71) Applicant: Conopco, Inc., Englewood Cliffs, NJ (US)

(72) Inventors: Prem Chandar, Closter, NJ (US); Guohui Wu, Woodbridge, CT (US); Nitish Kumar, Bihar (IN); Vamsi Krishna Manthena, Chattishgarh (IN); Kalpana Kamalakar Nayak, Bangalore (IN); Vibhav Ramrao Sanzgiri, Mumbai (IN); Anat Shiloach, Trumbull, CT (US)

(73) Assignee: CONOPCO, INC., Englewood Cliffs, NJ (US)

( * ) Notice: Subject to any disclaimer, the term of this patent is extended or adjusted under 35 U.S.C. 154(b) by 199 days.

This patent is subject to a terminal disclaimer.

(21) Appl. No.: 14/784,197

(22) PCT Filed: Apr. 9, 2014

(86) PCT No.: PCT/EP2014/057190
§ 371 (c)(1),
(2) Date: Oct. 13, 2015

(87) PCT Pub. No.: WO2014/170187
PCT Pub. Date: Oct. 23, 2014

(65) Prior Publication Data
US 2016/0053207 A1 Feb. 25, 2016

(30) Foreign Application Priority Data

Apr. 16, 2013 (IN) .................. 1430/MUM/2013

(51) Int. Cl.
A61L 2/23 (2006.01)
C11D 9/10 (2006.01)
C11D 3/48 (2006.01)
C11D 9/00 (2006.01)
C11D 9/26 (2006.01)
C11D 9/08 (2006.01)
C11D 9/12 (2006.01)

(52) U.S. Cl.
CPC ........ C11D 9/10 (2013.01); A61L 2/23 (2013.01);
C11D 3/48 (2013.01); C11D 9/00 (2013.01);
C11D 9/08 (2013.01); C11D 9/12 (2013.01);
C11D 9/26 (2013.01)

(58) Field of Classification Search
CPC ....................................................... A61L 2/23
See application file for complete search history.

(56) References Cited

U.S. PATENT DOCUMENTS

| 2,864,769 | A |   | 12/1958 | Lutz et al. |            |
|-----------|---|---|---------|-------------|------------|
| 3,050,467 | A |   | 8/1962  | Horowtiz et al. |        |
| 3,408,299 | A | * | 10/1968 | Henry ...... | C11D 9/20  |
|           |   |   |         |             | 510/396    |
| 4,017,573 | A | * | 4/1977  | Joshi ...... | B29C 47/046 |
|           |   |   |         |             | 264/102    |
| 4,861,489 | A | * | 8/1989  | Swift ...... | C02F 1/42  |
|           |   |   |         |             | 210/167.3  |
| 5,891,834 | A | * | 4/1999  | Chopra ..... | A61K 8/55  |
|           |   |   |         |             | 510/141    |
| 6,294,186 | B1|   | 9/2001  | Beerse et al. |          |
| 6,794,344 | B2|   | 9/2004  | Taylor et al. |          |
| 2006/0115440 | A1 |   | 6/2006 | Arata |              |
| 2008/0045491 | A1 |   | 2/2008 | Fitchmun |           |
| 2010/0098776 | A1 |   | 4/2010 | Carnali et al. |      |
| 2011/0223114 | A1 |   | 9/2011 | Chakrabortty et al. | |
| 2011/0224120 | A1 |   | 9/2011 | Meine et al. |        |
| 2012/0003413 | A1 |   | 1/2012 | Lesage et al. |       |
| 2012/0034314 | A1 |   | 2/2012 | Levison et al. |      |
| 2012/0201902 | A1 | * | 8/2012 | Modak ...... | A01N 31/02 |
|           |   |   |         |             | 424/618    |

FOREIGN PATENT DOCUMENTS

| CA | 586350 | 11/1959 |
| CA | 2335635 | 12/2000 |
| CN | 1500858 | 6/2004 |
| CN | 101659911 | 3/2010 |
| CN | 102186341 | 9/2011 |
| CN | 102559418 | 7/2012 |
| GB | 759950 | 10/1956 |
| GB | 847257 | 9/1960 |
| GB | 887247 | 1/1962 |
| JP | 8026956 | 1/1996 |
| JP | H08133918 | 5/1996 |
| JP | 9003492 | 1/1997 |
| JP | 2001039808 | 2/2001 |
| JP | 2004217581 | 8/2004 |
| JP | 2008512387 | 4/2008 |
| JP | 2009007266 | 1/2009 |
| JP | 2012509372 | 4/2012 |
| KR | 20000020781 | 4/2000 |
| KR | 20010069644 | 7/2001 |
| WO | WO9723594 | 7/1997 |
| WO | WO9840465 | 9/1998 |
| WO | WO9965317 | 12/1999 |
| WO | WO2006029213 | 3/2006 |
| WO | WO2011002929 | 1/2011 |
| WO | WO2011131422 | 10/2011 |

OTHER PUBLICATIONS

Feng et al. A mechanistic study of the antibacterial effect of silver ions on *Escherichia coli* and *Staphylococcus aureus*. Journal of Biomedical Materials Research. vol. 52, Issue 4. Oct. 2000.*
Keeping Hands Clean. Centers for Disease Control and Prevention (CDC). Feb. 1, 2011.*
Soap. Wikipedia. previous version from Apr. 5, 2012.*
Russell et al. Abstract: 7 Antimicrobial Activity and Action of Silver. Progress in Medicinal Chemistry vol. 31, 1994, pp. 351-370. 1994. (Year: 1994).*

(Continued)

*Primary Examiner* — Donald R Spamer
(74) *Attorney, Agent, or Firm* — Foley & Lardner LLP

(57) ABSTRACT

A soap bar comprising: (a) 25 to 85% by weight, based on the total weight of the bar, of fatty acid soap; (b) 0.1 to 100 ppm by weight, based on the total weight of the bar, of at least one silver (I) compound having a selected silver ion solubility, wherein at 25° C., a 1 wt % solution of the bar in water has a pH of from 9 to 11.

19 Claims, No Drawings

(56) References Cited

OTHER PUBLICATIONS

Search Report in PCTEP2014057189, dated Jun. 6, 2014.
Written Opinion in PCTEP2014057189, dated Jun. 6, 2014.
IPRP1 in PCTEP2014057189, dated Jul. 10, 2015.
IPRP1 in PCTEP2014057190, dated Jul. 3, 2015.
Search Report in EP13172451, dated Apr. 28, 2014, EP.
Search Report in EP13172455, dated Apr. 28, 2014, EP.
Search Report in PCTEP2014057190, dated Jul. 1, 2014.
Written Opinion 1 in PCTEP2014057190, dated Jul. 1, 2014.
Written Opinion 2 in PCTEP2014057189, dated Mar. 18, 2015.
Written Opinion 2 in PCTEP2014057190, dated Mar. 18, 2015.
Written Opinion in EP13172451, dated Apr. 28, 2014, EP.
Written Opinion in EP13172455, dated Apr. 28, 2014, EP.
Copending application for Chandar et al.; Case No. G6052USw; Filed: Oct. 13, 2015 entitled Liquid Soap Having Enhanced Antibacterial Activity.

\* cited by examiner

SOAP BAR HAVING ENHANCED ANTIBACTERIAL ACTIVITY

FIELD OF THE INVENTION

The subject invention relates to soap based cleansing compositions, in particular soap bars, having enhanced antibacterial activity against Gram positive and Gram negative microorganisms, as well as to methods of enhancing antibacterial activity against Gram positive and Gram negative microorganisms in skin cleaning applications having relatively short contact times.

BACKGROUND OF THE INVENTION

Soap compositions, for example, bars and liquids, are known to have antibacterial benefits largely associated with the removal of organisms from the skin through the cleansing/detergency action of such products. Additionally, such compositions commonly have biocidal action against many Gram negative bacteria. The biocidal action of soap compositions against Gram positive bacteria, such as for example S. aureus is, however, considerably more limited within the contact times typical of product use, generally under 1 minute, and more commonly on the order of 30 seconds or less. Achieving biocidal action against Gram positive bacteria is especially problematic in the case of high pH soap bars, by which is meant that a 1 wt. % solution thereof in water has a pH in a range of from 9 to 11 at 25° C.

Various routes to improving the biocidal activity of soap compositions have been suggested. For example, U.S. Pat. No. 6,794,344 (Taylor et al.) discloses soap bars that comprise at least about 50% soap having alkyl chain lengths of 8-10 carbon atoms, about 10% to about 30% hydric solvent, and free acid, preferably free fatty acid, such that the pH of a 10% aqueous solution of the soap bar is no greater than about 9. The soap bar is therein characterized as exhibiting, in the test therein described, a log reduction against Gram positive bacteria of at least 3 after 30 seconds of contact at 40° C., as measured against S. aureus. Information presented in Table 3 of Taylor et al. compares the effect of free fatty acid content as function of pH on antibacterial activity against S. aureus.

Routes to achieving an antimicrobial benefit in cleansing compositions, including soap-based compositions, as well as compositions based on synthetic anionic surfactant, i.e., "syndet", also include the use of one or more agents having a biocidal effect.

U.S. Patent Application Publication No. 2012/003413 (Levison et al.) discloses antiseptic formulations therein said to be capable of providing antimicrobial properties over an extended period of time. The formulations therein disclosed include chelated metal ions (including chelated silver ions) and a fixative polymer having the capacity to bond the chelated metal ions to the skin. In Table IV thereof, Levison et al. provides the formulation for a liquid soap based on synthetic anionic surfactant. The formulation includes, among other ingredients, sodium laureth sulfate, sodium lauryl sulphate, propylene glycol, cocamidopropyl betaine, cocamide DEA, ethyol alcohol, macadamia glycerides, acrylate cross polymer, silver dihydrogen citrate, and tetrasodium EDTA.

WO 01/1131422 discloses toilet soap therein characterized as having antimicrobic properties, which soap contains what is therein termed a "soap basis", functional additives, and bentonite powder intercalated with $Ag^+$ and/or $Cu^{2+}$ ions.

U.S. Patent Application. Publication No. 2010/0098776 (Carnali et al.) discloses soap-based liquid wash formulations therein said to have enhanced antibacterial activity, which compositions include from 0.01 to 10 wt. % antimicrobial agent, e.g., silver particles, zinc particles, copper particles or mixtures thereof. The soap-based formulations are said to include 10 to 50% by weight, preferably 25 to 40% by weight, more preferably 30 to 40% by weight of a fatty acid blend of $C_{12}$-$C_{18}$ fatty acids (the fatty acid blend being further characterized as having degrees of neutralization between 70% and 90%); 10 to 40% by weight of co-solvent such as, for example glycerol, ethylene glycol, propylene glycol, diethylene glycol, dipropylene glycol and mixtures thereof, and less than 18%, preferably less than 16% by weight water, such that the ratio of co-solvent to water lies in the range of 0.4-10, preferably 0.8 to 7, more preferably 1.0 to 5.

U.S. Pat. No. 3,050,467 (Horowitz et al.) discloses antiseptic cleaners (for example, soaps and detergents) that include a mixture of from about 90% to about 99% by weight of a water-soluble soap and from about 10% to about 1% by weight of a silver salt of partially depolymerized alginic acid. The recited amount of alginic acid is said to provide the compositions with a silver content of from 0.01 to 1% by weight.

U.S. Patent Application Publication No. 2006/0115440 (Arata et al.) discloses personal care products that include silver dihydrogen citrate and a physiologically acceptable medium. The compositions are said to include silver ion at a concentration of 50 ppb to 10,000 ppm, such concentrations being based on the total weight of silver ion per unit volume of the final composition (if liquid) or per unit weight of the final composition (if solid).

There remains a need for soap bars, in particular high pH soap bars that provide improved biocidal activity against Gram positive and Gram negative bacteria in the relatively short contact times typical of bar use.

SUMMARY OF THE INVENTION

It has now been found that the direct biocidal action, i.e., germ kill, of high pH soap bars against Gram positive and Gram negative bacteria including, for example, S. aureus, can be enhanced, within the short contact times associated with bar use, through the incorporation therein of selected silver(I) compounds, more particularly silver (I) compounds having a selected silver ion solubility value, as hereinafter more particularly described. Moreover, it has been found that such germ kill may be achieved using the silver(I) compounds at concentrations at which the compounds themselves, in water at comparable pH, i.e., 9 to 11, fail to provide effective biocidal activity within the desired short term contact times typical of soap bar applications, i.e., contact times of less than 1 minute, more particularly 30 seconds or less, even more particularly 10 seconds or less.

Without wishing to be bound by theory, the subject inventors have found that in the context of soap bar applications, the role of such low levels of the silver (I) compounds is to modify the environment of the microorganisms so as to enable the soap molecules to act as biocides. Thus, the subject invention is directed, in part, to enhancing the antibacterial activity of soap itself against Gram positive organisms.

Given the relatively high cost of silver, such low levels of silver compound provide for significant cost benefits, compared to the higher levels needed for the silver compounds themselves to have a significant biocidal effect within the contact times of interest. Additionally, the low levels of silver compound are desirable from both a sensory and processing vantage.

In one embodiment there is provided a soap bar comprising:
- (a) 25 to 85% by weight, based on the total weight of the bar, of fatty acid soap;
- (b) 0.1 to 100 ppm by weight, based on the total weight of the bar, of at least one silver (I) compound having a silver ion solubility (in water at 25° C.) of at least $1 \times 10^{-4}$ mol/L, wherein at 25° C., a 1 wt. % solution of the bar in water has a pH in a range of from 9 to 11, more particularly from 9.0 or 9.1 to 11.0, even more particularly from 9.5 to 10.8.

In a further embodiment there is provided a method of enhancing the antibacterial effectiveness against Gram positive bacteria of a high pH soap bar based on fatty acid soap, which comprises incorporating into the bar from 0.1 to 100 ppm by weight of at least one silver (I) compound having a silver ion solubility (in water at 25° C.) of at least $1 \times 10^{-4}$ mol/L, wherein the soap bar preferably provides a $Log_{10}$ Reduction against *S. aureus* ATCC 6538 of at least 2, preferably at least 3, more preferably at least 3.5, at a contact time of 30 seconds and even more preferably provides a $Log_{10}$ Reduction against *S. aureus* ATCC 6538 of at least 1, preferably at least 1.5, more preferably at least 2 at a contact time of 10 seconds, in the In Vitro Time-Kill Protocol hereinafter described.

In another embodiment there is provided a method of cleansing human skin, more particularly, a method of reducing Gram positive bacteria on human skin, which comprises;
- (i) lathering a high pH solid soap composition comprising:
  - (a) 25 to 85% by weight, based on the total weight of the bar, of fatty acid soap; and
  - (b) 0.1 to 100 ppm by weight, based on the total weight of the bar, of at least one silver (I) compound having a silver ion solubility (in water at 25° C.) of at least $1 \times 10^{-4}$ mol/L,
  to form an aqueous soap dilution containing the soap composition at a level of from 1 to 25%, by weight, based on the total weight of the dilution;
- (ii) applying the aqueous soap dilution to the skin for a period of less than 1 minute, more particularly up to 30 seconds, even more particularly up to 10 seconds; and
- (iii) rinsing the aqueous soap dilution from the skin.

In another embodiment, it has been found that when the solid soap compositions of the invention are further used in combination with essential oil actives thymol and terpineol, excellent antibacterial effect is obtained. Specifically, combinations of salt of silver with both thymol and terpineol have overall antibacterial effect against both Gram positive and Gram negative bacteria.

Each of thymol and terpineol are preferably present at a level of 0.01 to 2% by wt. of the total composition.

Preferably, the thymol and terpineol may be added to the silver-containing compositions of the invention as (a) an antimicrobial composition comprising 0.01 to 2% essential oil active mixture of thymol and terpineol and (b) a hydrotrope (preferably selected from the group consisting of sodium benzoate, sodium toluene sulphonate, sodium cumene sulphonate, sodium xylene sulphonate, sodium salicylate, sodium acetate and mixtures thereof).

Preferably, the silver-containing composition comprises 0.01 to 1% total thymol and terpineol. Additional essential oil actives, e.g., eugenol, geraniol or mixtures, can be used. Another preferred mixture of oils to be used in the silver-containing compositions, for enhanced antibacterial effect, is thymol, terpineol and eugenol.

DETAILED DESCRIPTION OF THE INVENTION

Except in the operating and comparative examples, or where otherwise explicitly indicated, all numbers in this description indicating amounts, parts, percentages, ratios, and proportions of material, physical properties of material, and conditions of reaction are to be understood as modified by the word "about". All parts, percentages, ratios, and proportions of material referred to in this description are by weight unless otherwise indicated.

The term "comprising" is meant not to be limiting to any subsequently stated elements but rather to encompass non-specified elements of major or minor functional importance. In other words, the listed steps, elements or options need not be exhaustive. Whenever the words "including" or "having" are used, these terms are meant to be equivalent to "comprising" as defined above. Where the compositions of the subject invention are described as "including" or "comprising" specific components or materials, narrower embodiments where the compositions can "consist essentially of" or "consist of" the recited components or materials are also contemplated.

It should also be noted that in specifying any range of concentration or amount, any particular upper concentration or amount can be associated with any particular lower concentration or amount.

As used herein the term "soap bar" is used interchangeably with the terms "solid soap composition" or "bar composition".

Throughout the specification and claims, all references to $log_{10}$ reduction in biocial activity against *Staphylococcus aureus* ATCC 6538, are to be understood as being pursuant to the In Vitro Time-Kill Protocol hereinafter described.

Fatty Acid Soaps

The term "fatty acid soap" or, more simply, "soap" is used here in its popular sense, i.e., salts of aliphatic alkane- or alkene monocarboxylic fatty acids preferably having 6 to 22 carbon atoms, and more preferably 8 to 18 carbon atoms. Reference to the fatty acid soap is to the fatty acid in neutralized form. Preferably the fatty acid from which the soap is derived is substantially completely neutralized in forming the fatty acid soap, that is say at least 95%, more particularly at least 98%, of the fatty acid groups thereof have been neutralized. In one or more embodiments it is preferred that the fatty acid soap is neutralized to an excess free alkali level of 0.01 to 0.05 wt %.

Fatty acid soap should comprise 25-85% by weight, preferably 40 to 80% by weight, even more preferably 50 to 75% by weight of the bar composition. Typical thereof are alkali metal or alkanol ammonium salts of fatty acids, although other metal salts thereof, e.g., magnesium salts, may also be employed. Sodium, potassium, magnesium, mono-, di- and tri-ethanol ammonium salts of such acids are among the more common soaps suitable for use herein. Commonly, sodium soaps are used in the compositions of this invention, but up to about 25% of the soap may be potassium or magnesium soaps.

As noted above, the fatty acids from which the soap salts are derived may contain unsaturation. The level of unsaturation should be in accordance with commercially acceptable standards. Excessive unsaturation is normally avoided to minimize color and odor issues. Commonly, not more than 40 wt. % of the fatty acids from which the soap salts are formed are unsaturated. In one or more embodiments, from 10 to 40 wt %, more particularly from 20 to 40 wt. %, of the fatty acids from which the soap salts are formed are unsaturated. In other embodiments, the fatty acids from which soap salts are formed are substantially free of unsaturation, i.e., less than 10 wt % of such fatty acids are unsaturated.

Soaps may be made by the classic kettle boiling process or modern continuous soap manufacturing processes wherein natural fats and oils such as tallow or coconut oil or their equivalents are saponified with an alkali metal hydroxide using procedures well known to those skilled in the art. Alternatively, the soaps may be made by neutralizing fatty acids, such as lauric (C12), myristic (C14), palmitic (C16), or stearic (C18) acids with an alkali metal hydroxide or carbonate. Coconut oil employed for the soap may be substituted in whole or in part by other "high-lauric" oils, that is, oils or fats wherein at least 50% of the total fatty acids are composed of lauric or myristic acids and mixtures thereof. These oils are generally exemplified by the tropical nut oils of the coconut oil class. For instance, they include: palm kernel oil, babassu oil, ouricuri oil, tucum oil, cohune nut oil, murumuru oil, jaboty kernel oil, khakan kernel oil, dika nut oil, and ucuhuba butter. In at least one embodiment, the soap is derived from coconut oil and/or mixtures of tallow and coconut oil, with the sodium salts thereof being of particular interest.

In one or more embodiments it is preferred that the combination of $C_{16}$ and $C_{18}$ fatty acids accounts for from 50 to 95 wt. % particularly from 55 to 90 wt. % of the fatty acids from which the soap salts are formed and, preferably, that the combination of $C_{12}$, $C_{16}$ and $C_{18}$ fatty acids accounts for from 85 to 99 wt. %, more particularly from 90 to 99 wt %, of the fatty acids from which the soap salts are formed. Preferably, the total amount of $C_8$ and $C_{10}$ fatty acids is less than 5 wt. %, and preferably is less than 3 wt. % of the fatty acids from which the soap salts are formed.

Silver Compounds

The silver compounds employed as component (b) of the subject bars are one or more water-soluble silver(I) compounds having a silver ion solubility at least $1.0 \times 10^{-4}$ mol/L (in water at 25° C.). Silver ion solubility, as referred to herein, is a value derived from a solubility product (Ksp) in water at 25° C., a well known parameter that is reported in numerous sources. More particularly, silver ion solubility [Ag+], a value given in mol/L may be calculated using the formula:

$$[Ag+]=(Ksp \cdot x)^{(1/(x+1))},$$

wherein Ksp is the solubility product of the compound of interest in water at 25° C., and x represents the number of moles of silver ion per mole of compound. It has been found that silver (I) compounds having a silver ion solubility of at least $1 \times 10^{-4}$ mol/L are suitable for use herein. Silver ion solubility values for a variety of silver compounds are given in Table 1:

TABLE 1

Silver ion Solubility Values

| Silver Compound | X | Ksp (mol/L in water at 25° C.) | Silver Ion Solubility [Ag+] (mol/L in water at 25° C.). |
|---|---|---|---|
| Silver nitrate | 1 | 51.6 | 7.2 |
| Silver acetate | 1 | $2.0 \times 10^{-3}$ | $4.5 \times 10^{-2}$ |
| Silver sulfate | 2 | $1.4 \times 10^{-5}$ | $3.0 \times 10^{-2}$ |
| Silver benzoate | 1 | $2.5 \times 10^{-5}$ | $5.0 \times 10^{-3}$ |
| Silver salicylate | 1 | $1.5 \times 10^{-5}$ | $3.9 \times 10^{-3}$ |
| Silver carbonate | 2 | $8.5 \times 10^{-12}$ | $2.6 \times 10^{-4}$ |
| Silver citrate | 3 | $2.5 \times 10^{-18}$ | $1.7 \times 10^{-4}$ |
| Silver oxide | 1 | $2.1 \times 10^{-8}$ | $1.4 \times 10^{-4}$ |
| Silver phosphate | 3 | $8.9 \times 10^{-17}$ | $1.3 \times 10^{-4}$ |
| Silver chloride | 1 | $1.8 \times 10^{-10}$ | $1.3 \times 10^{-5}$ |
| Silver bromide | 1 | $5.3 \times 10^{-13}$ | $7.3 \times 10^{-7}$ |
| Silver iodide | 1 | $8.3 \times 10^{-17}$ | $9.1 \times 10^{-9}$ |
| Silver sulfide | 2 | $8.0 \times 10^{-51}$ | $2.5 \times 10^{-17}$ |

Among the silver (I) compounds suitable for use herein are silver oxide, silver nitrate, silver acetate, silver sulfate, silver benzoate, silver salicylate, silver carbonate, silver citrate and silver phosphate, with silver oxide, silver sulfate and silver citrate being of particular interest in one or more embodiments. In at least one preferred embodiment the silver (I) compound comprises silver oxide.

In at least one embodiment the silver compound is not silver dihydrogen citrate. In another embodiment the silver compound is not a salt of alginic acid or substantially depolymerized alginic acid. In one preferred embodiment the silver compound is not in the form of nano particles, attached to nano particles or part of intercalated silicates such as, for example, bentonite.

Desirably, the silver (I) compound (b) is present in the subject bars at levels of 0.1-100 ppm by weight, more particularly 1-50 ppm by weight, even more particularly 5-20 ppm by weight, based on the total weight of the bar. Bars containing 5-15 ppm by weight of such silver (I) compound are of particular interest in one or more embodiments.

In a preferred embodiment, the silver-containing compositions of the invention are used in combination with essential oil antimicrobial actives thymol and terpineol. Preferably, each is present in overall silver-containing composition at level of 0.01 to 2% of the composition.

Thymol is preferably present in 0.02 to 0.5%, more preferably up to 0.3% by weight, further more preferably up to 0.2% by weight of the composition. Thymol may be added to the antimicrobial composition in purified form. Alternatively, thyme oil or thyme extract comprising thymol may be added to the antimicrobial composition, while ensuring that thymol is present in the desired concentration in the composition of the present invention. Thyme oil or thyme extract is obtained from the thyme plant. Thyme plant refers to a plant belonging be genus *Thymus* and includes but is not limited to the following species: *Thymus vulgaris, Thymus zygis, Thymus satureoides, Thymus mastichina, Thymus broussonetti, Thymus maroccanus, Thymus pallidus, Thymus algeriensis, Thymus serpyllum, Thymus pulegoide*, and *Thymus citriodorus*.

The structures of thymol and its isomer carvacrol are given below:

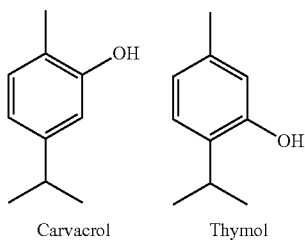

Carvacrol    Thymol

Terpineol is preferably present at 0.05 to 1%, more preferably up to 0.5% by weight of the composition. The terpineol is preferably selected from alpha-terpineol, beta-terpineol, gamma-terpineol or mixtures thereof. It is particularly preferred that the terpineol is alpha-terpineol. Terpineol may be added to the antimicrobial composition in purified form. Alternatively pine oil comprising terpineol may be added to the antimicrobial composition.

The structure of a terpineol compound is given below:

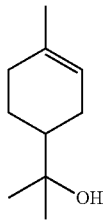

Optional Ingredients

The subject bars typically include one or more skin benefit agents. The term "skin benefit agent" is defined as a substance which softens or improves the elasticity, appearance, and youthfulness of the skin (stratum corneum) by either increasing its water content, adding, or replacing lipids and other skin nutrients, or both, and keeps it soft by retarding the decrease of its water content. Included among the suitable skin benefit agents are emollients, including, for example, hydrophobic emollients, hydrophilic emollients, or blends thereof.

Useful skin benefit agents include the following: (a) silicone oils and modifications thereof such as linear and cyclic polydimethylsiloxanes; amino, alkyl, alkylaryl, and aryl silicone oils; (b) fats and oils including natural fats and oils such as jojoba, soybean, sunflower, rice bran, avocado, almond, olive, sesame, persic, castor, coconut, and mink oils; cacao fat; beef tallow and lard; hardened oils obtained by hydrogenating the aforementioned oils; and synthetic mono-, di- and triglycerides such as myristic acid glyceride and 2-ethylhexanoic acid glyceride; (c) waxes such as carnauba, spermaceti, beeswax, lanolin, and derivatives thereof; (d) hydrophobic and hydrophilic plant extracts; (e) hydrocarbons such as liquid paraffin, petrolatum, microcrystalline wax, ceresin, squalene, pristan and mineral oil; (f) higher fatty acids such as lauric, myristic, palmitic, stearic, behenic, oleic, linoleic, linolenic, lanolic, isostearic, arachidonic and poly unsaturated fatty acids (PUFA); (g) higher alcohols such as lauryl, cetyl, stearyl, oleyl, behenyl, cholesterol and 2-hexydecanol alcohol; (h) esters such as cetyl octanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol monolaurate, glycerol distearate, glycerol tristearate, alkyl lactate, alkyl citrate and alkyl tartrate; (i) essential oils and extracts thereof such as mentha, jasmine, camphor, white cedar, bitter orange peel, ryu, turpentine, cinnamon, bergamot, citrus unshiu, calamus, pine, lavender, bay, clove, hiba, eucalyptus, lemon, starflower, thyme, peppermint, rose, sage, sesame, ginger, basil, juniper, lemon grass, rosemary, rosewood, avocado, grape, grape seed, myrrh, cucumber, watercress, calendula, elder flower, geranium, linden blossom, amaranth, seaweed, ginko, ginseng, carrot, guarana, tea tree, jojoba, comfrey, oatmeal, cocoa, neroli, vanilla, green tea, penny royal, aloe vera, menthol, cineole, eugenol, citral, citronelle, borneol, linalool, geraniol, evening primrose, camphor, thymol, spirantol, penene, limonene and terpenoid oils; (j) polyhydric alcohols, for example, glycerine, sorbitol, propylene glycol, and the like; and polyols such as the polyethylene glycols, examples of which are: Polyox WSR-205 PEG 14M, Polyox WSR-N-60K PEG 45M, or Polyox WSR-N-750, and PEG 7M; (k) lipids such as cholesterol, ceramides, sucrose esters and pseudo-ceramides as described in European Patent Specification No. 556,957; (l) vitamins, minerals, and skin nutrients such as milk, vitamins A, E, and K; vitamin alkyl esters, including vitamin C alkyl esters; magnesium, calcium, copper, zinc and other metallic components; (m) sunscreens such as octyl methoxyl cinnamate (Parsol MCX) and butyl methoxy benzoylmethane (Parsol 1789); (n) phospholipids; and (o) anti-aging compounds such as alpha-hydroxy acids and beta-hydroxy acids.

Skin benefit agents typically account for up to 45% by weight of the bar, with levels of from 1 to 15% by weight, more particularly from 1 to 8% by weight, being typical of the levels at which those skin benefit agents generally known as "emollients" are employed in the subject bars. Preferred skin benefit agents include fatty acids, hydrocarbons, polyhydric alcohols, polyols and mixtures thereof, with emollients that include at least one $C_{12}$ to $C_{18}$ fatty acid, petrolatum, glycerol, sorbitol and/or propylene glycol. Fatty acid emollients, when present, are distinguished from the fatty acid soap component of the subject bars. When present, the total amount of free fatty acid typically does not exceed 5% by weight of the subject bars.

Additional optional ingredients which may be present in the subject bars are, for example: fragrances; sequestering and chelating agents such as tetrasodium ethylenediaminetetraacetate (EDTA), ethane hydroxyl diphosphonate (EHDP), and etidronic acid, aka 1-hydroxyethylidene diphosphonic acid (HEDP); coloring agents; opacifiers and pearlizers such as zinc stearate, magnesium stearate, $TiO_2$, ethylene glycol monostearate (EGMS), ethylene glycol distearate (EGDS), or Lytron 621 (Styrene/Acrylate copolymer) and the like; pH adjusters; antioxidants, for example, butylated hydroxytoluene (BHT) and the like; preservatives; stabilizers; antimicrobials/preservatives such as, for example, 2-hydroxy-4,2',4' trichlorodiphenylether (Triclosan), dimethyloldimethylhydantoin (Glydant XL1000), parabens, sorbic acid, thymol, and terpineol to name a few (with combinations of thymol and terpineol as described, for example, in U.S. Patent Application Publication No. 2011/0223114 incorporated herein by reference, being of particular interest in one or more embodiments); suds boosters, such as for example, coconut acyl mono- or diethanol amides; ionizing salts, such as, for example, sodium chloride and sodium sulfate, and other ingredients such as are conventionally used in soap bars. The total amount of such additional optional ingredients is typically from 0 to 15% by weight, more particularly from 0.01 to 10% by weight, based on the total weight of the bar.

Bar Manufacture

The bars described in this application can be prepared using manufacturing techniques described in the literature and known in the art for the manufacture of soap bars. Examples of the types of manufacturing processes available are given in the book Soap Technology for the 1990's (Edited by Luis Spitz, American Oil Chemist Society Champaign, Ill. 1990). These broadly include: melt forming, extrusion/stamping, and extrusion, tempering, and cutting. A preferred process is extrusion and stamping because of its capability to economically produce high quality bars.

The soap bars may, for example, be prepared by either starting with or forming the soap in situ. When employing the fatty acid or acids that are the precursors of the soap as starting ingredients, such acid or acids may be heated to temperature sufficient to melt same, typically at least 80° C. and, more particularly from 80° C. to below 100° C., and neutralized with an suitable neutralizing agent or base, for example, sodium hydroxide, commonly added as a caustic solution. The neutralizing agent is preferably added to the melt in an amount sufficient to fully neutralize the soap-forming fatty acid and, in at least one embodiment, is preferably added in an amount greater than that required to substantially completely neutralize such fatty acid, for example an amount of 0.01-0.05 wt % greater than that needed for full neutralization.

Following neutralization, excess water may be evaporated and additional composition components, including silver (I) compound added. Desirably water content is reduced to a level such that, based on the total weight thereof, the resulting bars contains no more that 25% by weight, preferably no more than 20% by weight, more preferably no more than 18% by weight of water, with water contents of from 8 to 15% by weight being typical of many bars. In the course of processing, either as part of neutralization and/or subsequent thereto, the pH may be adjusted, as needed, to provide the high pH desired for the subject bars.

The resulting mixture may be formed into bars by pouring the mixture, while in a molten state into molds or, by amalgamation, milling, plodding and/or stamping procedures as are well known and commonly employed in the art. In a typical process, the mixture is extruded through a multi-screw assembly and the thick liquid that exits therefrom, which typically has a viscosity in the range of 80,000 to 120,000 cPs, is made to fall on rotating chilled rolls. When the viscous material falls on the chilled rolls, flakes of soap are formed. These flakes are then conveyed to a noodler plate for further processing. As the name suggests, the material emerging from this plate is in the form of noodles. The noodles are milled, plodded and given the characteristic shape of soap bars.

The bars may also be made by melt cast processes and variations thereof. In such processes, saponification is commonly carried out in an ethanol-water mixture (or the saponified fatty acid is dissolved in boiling ethanol). Following saponification other components may be added, and the mixture is preferably filtered, poured into molds, and cooled. The cast composition then undergoes a maturation step whereby alcohol and water are reduced by evaporation over time. Maturation may be of the cast composition or of smaller billets, bars or other shapes cut from same. In a variation of such process described in U.S. Pat. Nos. 4,988,453 and 6,730,643, incorporated herein by reference, saponification is carried out in the presence of polyhydric alcohol and water, with the use of volatile oil in the saponification mixture being reduced or eliminated. Melt casting allows for the production of translucent or transparent bars, in contrast to the opaque bars typically produced by milling or other mechanical techniques.

In one or more embodiments, the subject bars have a penetration value of from 0.1 mm to 4 mm, preferably from 1 mm to 3 mm. Penetration value is determined using a penetrometer fitted with a weighted, moveable cone (150 g±0.1 g), the cone being further characterized as having a cone angle: of 32.2°, a height of 16 mm, and base width of 9.3 mm; such an instrument is available from Adair Dutt and Company. The sample to be measured is equilibrated to 25° C. and positioned under the cone such that the cone tip just touches the sample surface; the cone is then is released and allowed to fall freely, and its distance of penetration into the sample in a period of 5 seconds is measured to the nearest 0.1 mm. The test is repeated three times, allowing at least 5 mm distance between each measurement position on the sample. The average of the three repeat tests is the penetration value. A higher value indicates a softer bar.

The soap compositions of this invention are of interest with respect to biocidal activity against Gram positive bacteria, including in particular S. aureus. Other Gram positive bacteria against which the soap compositions are of interest are S. epidermidis, and/or Corynebacteria, in particular, Corynebacteria strains responsible for the hydrolysis of axilla secretions to malodorous compounds. Desirably, the bar provides a $\log_{10}$ reduction in biocial activity against Staphylococcus aureus ATCC 6538 of at least 2, preferably at least 3 more preferably at least 3.5 at a contact time of 30 seconds, and even more preferably provides a $\text{Log}_{10}$ Reduction against S aureus ATCC 6538 of at least 1, preferably at least 1.5 more preferably at least 2 at a contact time of 10 seconds.

In use, the bars are diluted with water to form what is typically a 1 to 25 wt % solution thereof in water, and the resulting soap solution applied to the skin for contact times under 1 minute, typically 30 seconds or less (with contact times of 10 to 30 seconds being of interest with respect to contact times of a moderate to relatively long duration, and contact times of 10 seconds or less being of interest with respect to contact times of short to moderate duration), and thereafter is removed from the skin, typically by rinsing with water. Preferably the bars have a lather volume of at least 200 ml following the procedure of Indian Standard 13498: 1997, Annex C, incorporated herein by reference.

EXAMPLES

The following non-limiting examples are provided to further illustrate the invention; the invention is not in any way limited thereto. The following protocol was used to evaluate biocidal activity.

In-Vitro Time-Kill Protocol

Soap Solution Preparation

The solid soap bar being evaluated is mixed with water and dissolved at 50° C. to give a 10 wt % solution. After dissolution, the resulting soap bar solution is equilibrated at 46° C. prior to performing the bactericidal assay procedure.

Bacteria

Staphylococcus aureus ATCC 6538, were used in this study to represent Gram positive bacteria. The bacteria was stored at −80° C. Fresh isolates were cultured twice on Tryptic Soy Agar plates for 24 hours at 37° C. before each experiment.

In-Vitro Time-Kill Assay

Time-kill assays are performed according to the European Standard, EN 1040:2005 entitled "Chemical Disinfectants and Antiseptics—Quantitative Suspension Test for the Evaluation of Basic Bactericidal Activity of Chemical Disinfectants and Antiseptics—Test Method and Requirements (Phase 1)", incorporated herein by reference. Following this procedure Growth-phase bacterial cultures at $1.5 \times 10^8$ to $5 \times 10^8$ colony forming units per ml (cfu/ml) are treated with the 10 wt. % soap bar solutions (prepared as described above) at 46° C.

In forming the test samples, 8 parts by weight of the 10 wt. % soap bar solution is combined with 1 part by weight of the culture and 1 part by weight of water, i.e., the concentration of the soap bar composition in the test samples is 8 wt. %. After 10, 30, and 60 seconds of exposure, samples are neutralized to arrest the antibacterial activity of the soap solutions. The resulting solutions are serially diluted, plated on solid medium, incubated for 24 hours and surviving cells are enumerated. Bactericidal activity is defined as the log reduction in cfu/ml relative to the bacterial concentration at 0 seconds. Cultures not exposed to any soap or silver solutions serve as no-treatment controls.

The $\log_{10}$ reduction is calculated using the formula:

$$\text{Log}_{10} \text{ Reduction} = \log_{10} (\text{numbers control}) - \log_{10} (\text{test sample survivors})$$

Examples 1 to 13 and Comparative Examples A to E

Soap bars were prepared according to formulations as indicated in Table 2 below.

TABLE 2

| Ingredient (wt. %) | Soap Bar I | Soap Bar II |
|---|---|---|
| Anhydrous Sodium Soap (85 wt. % tallow soap/15 wt. % coconut soap) | 68.04 | 68.04 |
| Soda Ash | 0.5 | 0.5 |
| C10-18-alpha olefin-sulfonate (90 wt. % in water) | 1.1 | 1.1 |
| Talc | 6.0 | 6.0 |
| Glycerine | 6.0 | 6.0 |
| Sodium Chloride | 0.8 | 0.8 |
| Etidronic Acid | 0.1 | 0.10 |
| Tetrasodium EDTA | 0.04 | 0.04 |
| Silver Compound | As indicated in Table 3 | 0 |
| Water | To 100% | To 100% |
| pH (as a 1 wt % aqueous solution) | 10.7 | 10.7 |

The biocidal activity of the bars so produced was evaluated following the above described protocol. Also evaluated were aqueous solutions of silver compound, formulated to a pH comparable to that of the soap solution (i.e., pH 10.7). Biocidal activity results are reported in Tables 3 to 5. Silver levels reported in Examples 1 to 3 are based on the weight percent of silver compound in the soap bar. Silver levels reported in Comparative Examples A and B are reported as the levels of silver in the test solution prior to the combination of 8 parts by weight thereof with one part by weight of culture and 1 part by weight of water.

TABLE 3

Biocidal Activity $\text{Log}_{10}$ Reduction
against *S. aureus* ATCC 6538
(Average ± S.D.)

| | | Contact Time | | |
|---|---|---|---|---|
| Example | Composition | 10 Seconds | 30 Seconds | 60 Seconds |
| 1 | Soap bar I with 0.01 wt. % $Ag_2SO_4$* | 2.0 ± 0.5 | 4.1 ± 0.4 | >4.2 |
| 2 | Soap bar I with 0.001 wt. % $Ag_2SO_4$** | 1.2 ± 0.5 | 3.5 ± 0.6 | >4.1 |
| 3 | Soap bar I with 0.001 wt % $Ag_2O$*** | 1.5 ± 0.2 | 3.1 ± 0.3 | >4.2 |
| A (Comp.) | 0.001 wt % $Ag_2SO_4$ | 0.3 ± 0.3 | 0.3 ± 0.3 | 0.4 ± 0.2 |
| B (Comp.) | 0.0001 wt. % $Ag_2O$ | −0.1 ± 0.1 | 0.1 ± 0.2 | 0.2 ± 0.1 |
| C (Comp.) | Soap bar II (no silver compound) | 0.3 ± 0.1 | 0.7 ± 0.2 | 1.7 ± 0.3 |

*10 wt. % soap bar solution contained 0.001 wt. % $Ag_2SO_4$.
**10 wt. % soap bar solution contained 0.0001 wt. % $Ag_2SO_4$.
***10 wt/% soap bar solution contained 0.0001 wt. % $Ag_2O$.

As demonstrated by the Table 3 data, Comparative Example A failed to provide a significant biocidal effect at contact times of 10, 30 and 60 seconds. Likewise, Comparative Example C failed to provide a significant biocidal effect at contact times of 10 and 30 seconds. In contrast, Examples 1 to 3 demonstrate that the combination of soap and silver compound ($Ag_2SO_4$ or $Ag_2O$) provides a synergistic effect with respect to biocidal activity at contact times of 10, 30 and 60 seconds.

The next series of Examples, reported in Table 4, compares the biocidal effects of soap bar solutions to which silver compound is post-added at a constant level (0.001 wt. % of the soap bar solution). Test samples were prepared by combining 8 parts by weight of a given soap bar solution with 1 part by weight of culture and 1 part by weight of water. The reported soap bar contents are based on the soap bar content of the final test samples. The level of silver compound in Comparative Example D is the amount of silver in the solution prior to the combination of 8 parts by weight thereof with 1 part by weight of culture and 1 part by weight of water. Biocidal activity of the test samples is evaluated as described above.

TABLE 4

Biocidal Activity
*S. aureus* ATCC 6538 $\text{Log}_{10}$ Reduction
(Average ± S.D.)

| | | Contact Time | | |
|---|---|---|---|---|
| Example | Composition | 10 Seconds | 30 Seconds | 60 Seconds |
| D (Comp.) | 0.001% $Ag_2SO_4$ | 0.0 ± 0.1 | 0.1 ± 0.2 | 0.3 ± 0.4 |
| Example 4 | 1 wt % Soap bar II/0.001% $Ag_2SO_4$ | 0.7 ± 0.1 | 2.7 ± 0.1 | >3.9 |
| Example 5 | 2 wt % Soap bar II/0.001% $Ag_2SO_4$ | 1.3 ± 0.1 | 3.0 ± 0.2 | >4.1 |
| Example 6 | 3 wt % Soap bar II/0.001% $Ag_2SO_4$ | 1.4 ± 0.2 | 3.1 ± 0.2 | >3.9 |
| Example 7 | 4 wt % Soap bar II/0.001% $Ag_2SO_4$ | 1.4 ± 0.1 | 3.4 ± 0.2 | >4.1 |

TABLE 4-continued

Biocidal Activity
S. aureus ATCC 6538 $Log_{10}$ Reduction
(Average ± S.D.)

| | | Contact Time | | |
|---|---|---|---|---|
| Example | Composition | 10 Seconds | 30 Seconds | 60 Seconds |
| Example 8 | 6 wt % Soap bar II/0.001% $Ag_2SO_4$ | 1.8 ± 0.2 | 3.6 ± 0.1 | >4.1 |
| Example 9 | 8 wt % Soap bar II/0.001% $Ag_2SO_4$ | 1.9 ± 0.1 | 3.9 ± 0.3 | >4.1 |

As demonstrated by the Table 4 data, a synergistic effect is observed for each of the soap bar levels tested.

Table 5 compares the biocidal activity of soap bar solutions containing different post added-silver compounds. Silver compound was post added at the reported levels to 10 wt. % solutions of soap bar II in water. Test samples (prepared by combining 8 parts by weight of silver compound-containing soap bar solution with 1 part by weight of culture and 1 part by weight of water) were evaluated as described above.

TABLE 5

Biocidal Activity
S. aureus ATCC 6538 $Log_{10}$ Reduction
(Average ± S.D.)

| | Silver Ion Solubility [Ag+] (mol/L in | | Contact Time | | |
|---|---|---|---|---|---|
| Example | water at 25° C.). | Composition | 10 Seconds | 30 Seconds | 60 Seconds |
| E (Comp.) | $1.3 \times 10^{-5}$ | Soap bar II/ 0.001% AgCl | 0.3 ± 0.2 | 1.7 ± 0.2 | 3.1 ± 0.2 |
| 10 | $2.6 \times 10^{-4}$ | Soap bar II/ 0.001% $Ag_2CO_3$ | 2.6 ± 0.5 | 3.7 ± 0.1 | >3.8 |
| 11 | $4.5 \times 10^{-2}$ | Soap bar II/ 0.001% Ag Acetate | 2.6 ± 0.5 | >3.8 | >3.8 |
| 12 | $1.7 \times 10^{-4}$ | Soap bar II/ 0.001% Ag Citrate | 2.3 ± 0.5 | >3.8 | >3.8 |
| 13 | 7.2 | Soap bar II/ 0.001% $AgNO_3$ | 2.5 ± 0.5 | >3.8 | >3.8 |

Comparative Example E which included soap and silver chloride (a silver compound having a silver ion solubility in water at 25° C. of $1.3 \times 10^{-5}$ mol/L (a value under $1 \times 10^{-4}$ mol/L)) lacked significant biocidal activity at a contact time of 10 seconds. At contact times of 30 and 60 seconds, Comparative Example E had significantly lower biocidal activity than the soap/silver compositions of Examples 10 to 13, which contained silver compounds of higher silver ion solubility.

The invention claimed is:

1. A soap bar comprising:
   (a) 25 to 85% by weight, based on the total weight of the bar, of fatty acid soap;
   (b) 0.1 to 100 ppm by weight, based on the total weight of the bar, of at least one silver (I) compound having a silver ion solubility in water at 25° C. of at least $1 \times 10^{-4}$ mol/L,
   wherein at 25° C., a 1 wt % solution of the bar in water has a pH in a range of from 9 to 11.

2. The bar according to claim 1 wherein component (b) is one or more silver compounds selected from one group consisting of silver oxide, silver nitrate, silver acetate, silver sulfate, silver benzoate, silver salicylate, silver carbonate, silver citrate and silver phosphate.

3. The bar according to claim 1 wherein the silver (I) compound comprises silver oxide.

4. The bar according to claim 1 wherein the fatty acid soap comprises an alkali metal salt of aliphatic alkane- and/or alkene monocarboxylic acids having 8 to 18 carbon atoms.

5. The bar according to claim 1 wherein component (b) is one or more silver compounds selected from one group consisting of silver oxide, silver sulfate and silver citrate.

6. The bar according to claim 1 wherein component (b) is present in an amount of 1 to 50 ppm by weight, based on the total weight of the bar.

7. The bar according to claim 1 wherein component (b) is present in an amount of 5 to 20 ppm by weight, based on the total weight of the bar.

8. The bar according to claim 1 wherein the fatty acid soap (a) has been neutralized to an excess free alkali level of 0.01 to 0.05 wt %.

9. A method of reducing Gram positive bacteria on human skin, which comprises;
   (i) lathering a high pH solid soap composition to form an aqueous soap dilution containing the high pH solid soap composition at a level of from 1 to 25% by weight, based on the total weight of the dilution,
      wherein the high pH solid soap composition comprises:
         (a) 25 to 85% by weight, based on the total weight of the high pH solid soap composition, of fatty acid soap; and
         (b) 0.1 to 100 ppm by weight, based on the total weight of the high pH solid soap composition, of at least one silver(I) compound having a silver ion solubility in water at 25° C. of at least $1 \times 10^{-4}$ mol/L,
      wherein a 1% solution of said high pH solid soap composition has a pH of from 9 to 11;
   (ii) applying the aqueous soap dilution to the skin for a contact time of less than 1 minute; and
   (iii) rinsing the aqueous soap dilution from the skin;
   wherein the method provides a $log_{10}$ reduction in biocidal activity against Gram positive bacteria.

10. The method according to claim 9 wherein the aqueous soap dilution is applied to the skin for a contact time of not more than 30 seconds.

11. The method of claim 10 wherein the high pH solid soap composition comprises from 1 to 50 ppm by weight of the silver (I) compound.

12. The method according to claim 9 wherein a 1 wt. % solution of the high pH solid soap composition in water has a pH of from 9.5 to 10.8.

13. The method of claim 10, wherein the contact time period is from 10 to 30 seconds.

14. The method according to claim 9, wherein the high pH solid soap composition provides a $\log_{10}$ reduction in biocidal activity against *Staphylococcus aureus* ATCC 6538 of at least 2 at a contact time of 10 seconds.

15. The method according to claim 9, wherein the high pH solid soap composition provides a $\log_{10}$ reduction in biocidal activity against *Staphylococcus aureus* ATCC 6538 of at least 3 at a contact time of 10 seconds.

16. The method according to claim 9, wherein the silver (I) compound is selected from the group consisting of silver oxide, silver nitrate, silver acetate, silver sulfate, silver benzoate, silver salicylate, silver carbonate, silver citrate and silver phosphate.

17. A soap bar comprising:
(a) 25 to 85% by weight, based on the total weight of the bar, of fatty acid soap;
(b) 0.1 to 100 ppm by weight, based on the total weight of the bar, of at least one silver (I) compound having a silver ion solubility in water at 25° C. of at least $1 \times 10^{-7}$ mol/L,
wherein:
    a 1 wt % solution of the bar in water at 25° C. has a pH in a range of from 9 to 11; and
    the silver (I) compound is selected from the group consisting of silver oxide, silver nitrate, silver acetate, silver sulfate, silver carbonate, silver citrate and silver phosphate.

18. The bar according to claim 17, wherein the fatty acid soap comprises an alkali metal salt of aliphatic alkane- and/or alkene monocarboxylic acids having 8 to 18 carbon atoms.

19. The bar according to claim 17, wherein the fatty acid soap (a) has been neutralized to an excess free alkali level of 0.01 to 0.05 wt %.

* * * * *